United States Patent [19]

Otto et al.

[11] 4,195,029
[45] Mar. 25, 1980

[54] PROCESS FOR PRODUCING ORGANOTIN COMPOUNDS

[75] Inventors: Eberhard Otto, Lindenfels; Wolfgang Wehner, Zwingenberg; Hermann O. Wirth, Bensheim, all of Fed. Rep. of Germany

[73] Assignee: Ciba-Geigy Corporation, Ardsley, N.Y.

[21] Appl. No.: 958,761

[22] Filed: Nov. 8, 1978

[30] Foreign Application Priority Data

Nov. 14, 1977 [SE] Sweden .............................. 7713867

[51] Int. Cl.² .............................................. C07F 7/22
[52] U.S. Cl. ................................................. 260/429.7
[58] Field of Search ................................... 260/429.7

[56] References Cited
U.S. PATENT DOCUMENTS

| | | | |
|---|---|---|---|
| 3,440,255 | 4/1969 | Matsuda et al. | 260/429.7 |
| 3,607,893 | 9/1971 | Reifenberg et al. | 260/429.7 |
| 4,080,363 | 3/1978 | Hutton et al. | 260/429.7 |
| 4,105,684 | 8/1978 | Hutton et al. | 260/429.7 |

OTHER PUBLICATIONS

Chemical Abstracts 85 1094426 (1976).
Chemical Abstracts 86 44403p (1977).

*Primary Examiner*—Helen M. S. Sneed
*Attorney, Agent, or Firm*—Luther A. R. Hall

[57] ABSTRACT

A process for producing organotin compounds of the formula I $$X_3Sn-\underset{\underset{R}{|}}{\overset{\overset{R}{|}}{C}}-\overset{R}{\underset{|}{CH}}-\overset{O}{\underset{}{\overset{\|}{C}}}-Y \quad (I)$$

in which
X is a chlorine, bromine or iodine atom, the
R's independently of one another are each a hydrogen atom or alkyl, and
Y is OH, NH$_2$ or OR', wherein
R' is a hydrocarbon group which optionally contains a functional group and which is of aliphatic, cycloaliphatic or aromatic character, by the direct reaction of a tin dihalide with an unsaturated nitrile of the formula II $$\underset{\underset{R}{|}}{\overset{\overset{R}{|}}{C}}=\overset{R}{\underset{|}{C}}-CN \quad (II),$$

in which R has the aforesaid meaning, and with hydrogen chloride, hydrogen bromide or hydrogen iodide, in which process the reaction is performed in the presence of water, of a carboxylic acid, or of water and alcohol, or of at least 3 mols of alcohol per mol of nitrile.

16 Claims, No Drawings

PROCESS FOR PRODUCING ORGANOTIN COMPOUNDS

The present invention relates to a process for producing carbofunctional organotin compounds.

Organotin compounds are of considerable industrial importance as stabilisers for halogen-containing thermoplasts. There have recently also been suggested carbofunctional organotin compounds. Various possibilities exist for producing stabilisers of this type.

Thus, for example, in the German Offenlegungsschrift No. 1,963,569 it is mentioned in a general manner that halogenostannic acid reacts with olefines in the presence of polar solvents, and the olefine can contain functional groups. Acrylonitrile is named as an example. It has however been found that in this reaction the desired compound is obtained in insufficient yields. Furthermore, undesirable secondary reactions occur in this process.

Monoorganotin compounds are accessible also by a process suggested in the German Offenlegungsschrift No. 2,540,210. They are produced by way of the reaction of tin dihalides with hydrogen chloride and a suitable olefine. The process described herein is limited however to olefines which contain a carbonyl group in conjugation with the double bond. This process cannot be readily applied to other substituted vinyl compounds, for example nitriles.

There exists however a need for economical processes for producing monoorganotin derivatives using readily obtainable starting compounds, such as acrylonitrile. It was therefore the object of the present invention to provide an economical process for producing carbofunctional organotin compounds.

The subject matter of the present invention is a process for producing organotin compounds of the formula I

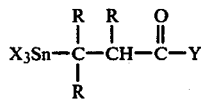  (I)

in which
X is a chlorine, bromine or iodine atom, the
R's independently of one another are each a hydrogen atom or alkyl, and
Y is OH, NH$_2$ or OR', wherein R' is a hydrocarbon group which optionally contains a functional group and which is of aliphatic, cycloaliphatic or aromatic character, by the direct reaction of a tin dihalide with an unsaturated nitrile of the formula

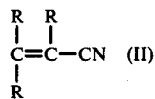  (II), in which R has the aforesaid meaning, and with hydrogen chloride, hydrogen bromide or hydrogen iodide, in which process the reaction is performed in the presence of water, of a carboxylic acid, or of water and alcohol, or of at least 3 mols of alcohol per mol of nitrile.

For mainly economical reasons, X is a chlorine atom. R is preferably hydrogen and/or alkyl having 1 to 4 C atoms, particularly hydrogen and/or methyl, the reason for this preferance being the readily accessible nitriles: acrylonitrile, methacrylonitrile, crotononitrile and β-dimethylacrylonitrile.

As a hydrocarbon group, R' can be: straight-chain or branched-chain alkyl, unsubstituted or substituted cycloalkyl, cycloalkylalkyl, aryl and aralkyl, with the substituent preferably being alkyl which can contain functional groups. Preferably, cycloalkyl is cyclohexyl, aryl is phenyl, and aralkyl is benzyl. R' preferably contains 1 to 12 C atoms and is in particular, as preferred subgroup, cycloalkyl or straight-chain or branched-chain alkyl.

If R' is substituted by functional groups, these are for example: hydroxyl, mercapto, alkoxy, alkylthio, carboxyl and alkoxycarbonyl.

Examples of R' are: methyl, ethyl, n- or i-propyl, n-, i- and t-butyl, pentyl, hexyl, heptyl, 2-hexyl, 3-heptyl, octyl, 2-ethylhexyl, nonyl, decyl, undecyl, dodecyl, cyclopentyl, cyclohexyl, methylcyclohexyl, cyclohexylmethyl, methylcyclohexylmethyl, phenyl, methylphenyl, ethylphenyl, butylphenyl, octylphenyl, naphthyl, benzyl, methylbenzyl, octylbenzyl or α- or β-phenylethyl.

Examples of R' having functional groups are: β-hydroxyethyl, β-mercaptoethyl, methoxyethyl, butoxyethyl, octoxyethyl, methylthioethyl, propylthioethyl, methoxycarbonyl, β-ethoxycarbonyl as well as alkoxycarbonylalkyl, for example methoxycarbonylmethyl, ethoxycarbonylpropyl, butoxycarbonylethyl and dodecyloxycarbonylmethyl.

Among the carboxylic acids used according to the invention, those are preferred which have 1 to 12 C atoms; they can also be aromatic, for example benzoic acid. Particularly preferred are the carboxylic acids which are readily volatile or which form readily volatile acid halides, such as propionic acid, acetic acid and particularly formic acid.

In the production process according to the invention, the tin dihalide can be used in various forms, for example as melted-down anhydrous salt in the form of flakes or lamella, or as dried salt in powder or dust form. It is also possible to perform the reaction in the excess reactant (alcohol, acid, water and/or nitrile), or in an additional solvent. Suitable solvents for this purpose are inert solvents, for example those with ether, carboxylic acid ester, keto or sulfone functions, or hydrocarbons as well as halogenated hydrocarbons, for example methylene chloride or chloroform, and also acid amides such as dimethylformamide. In order to avoid transesterifications, the ester function advantageously contains the radical of an alcohol, which is also used as reactant.

In the reaction according to the invention, importance is to be attached to ensuring that there is present, besides the unsaturated nitrile, water, a carboxylic acid or water and alcohol, preferably in at least the molar ratio. There can however be present slightly less than the equivalent amount of nitrile.

If the unsaturated nitrile and water are used in the molar ratio of about 1:1 to 1:2, there are obtained tin halides wherein Y in the formula I is NH$_2$. These tin halides with an acid amide function are also formed when nitrile and carboxylic acid are used at least in the molar ratio of 1:1, with the corresponding carboxylic acid anhydride or carboxylic acid halide, or CO with the use of formic acid, being formed, which is removed from the reaction mixture.

Where the unsaturated nitrile and water (also in the form of aqueous HCl) are used in the molar ratio greater than 1:2, tin halides having a carboxylic acid function (Y=OH) are obtained. If the unsaturated nitrile, water and alcohol are used in the molar ratio of 1:1:1, there are obtained tin halides having a carboxylic acid ester function (Y=OR′), which moreover are also obtained if the unsaturated nitrile and alcohol are used in the molar ratio of at least 1:3. This last-mentioned variant is preferably performed with low alcohols in order to obtain correspondingly readily volatile ethers or halogenated hydrocarbons, which are formed in this reaction. There are preferably used aliphatic or cycloaliphatic alcohols having 1 to 12, especially 1 to 6, C atoms. Also phenols, particularly alkylphenols, can be used.

The reaction temperature is in general −30° to 100° C., preferably 20° to 50° C. The reaction is advantageously performed under normal pressure or under a slight excess pressure.

The procedure consists of placing the tin dihalide and the reactants, with or without solvent, into the reaction vessel, and subsequently feeding in the hydrogen halide (preferably hydrogen chloride).

It is however also possible to put the tin dihalide and the solvent into the reaction vessel, and to then simultaneously introduce the reactants and the hydrogen chloride gas. It is advantageous in this case to operate using the counterflow principle, whereby also a continuous performance of the process is possible.

According to a further embodiment, the process can be performed in stages by firstly producing in a suitable solvent trichlorostannane, and then reacting it with the unsaturated nitrile in the presence of an alcohol. The trichlorostannane can be produced in this case by reacting hydrogen chloride with tin dihalide or tin in polar solvents, especially in ethers.

By the process according to the invention there are surprisingly obtained valuable organotin compounds in a simple manner, economically in high yields, and under very mild reaction conditions, and readily available and cheap raw materials can be used as starting materials. In the reaction, the tin(II) halide used is surprisingly largely converted into the desired organotin compounds.

The organotin compounds produced according to the invention can be used as biocides or as catalysts for producing polyurethane. They are particularly suitable however as intermediates for organotin stabilisers, with which halogen-containing thermoplasts are stabilised. Further details in this respect are given in the German Offenlegungsschriften Nos. 2,607,178 and 2,540,210.

The following Examples serve to further illustrate the invention. The term 'parts' denotes parts by weight.

EXAMPLE 1

Hydrogen chloride gas is passed into a mixture of 37.9 parts of anhydrous tin dichloride, 10.6 parts of acrylonitrile and 70 parts of absolute ethanol. The supply of gas is so regulated that a reaction temperature of 40° to 50° C. is established. The time until saturation with hydrogen chloride gas is attained is 4 hours. The volatile constituents are removed in vacuo to leave a crystalline product which, according to the $^1$HMR spectrum, consists principally of

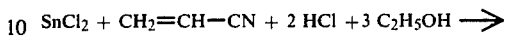

The reaction proceeds probably according to the following gross equation:

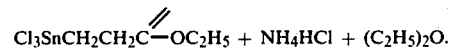

EXAMPLE 2

190 parts of tin(II)chloride (anhydrous) and 74 parts of n-butanol are placed into a four-necked flask fitted with stirrer, reflux condenser, thermometer and gas-inlet tube. Stirring is maintained as a stream of dry hydrogen chloride gas is passed into the flask at 40° C., whilst simultaneously a solution of 53 parts of acrylonitrile and 18 parts of water in 200 parts of n-butanol is added dropwise. After 5 hours, the ammonium chloride, formed as a result of saponification of the nitrile, is filtered off. Excess n-butanol is distilled off from the filtrate. There are obtained 348 parts of the monoorganotin compounds $Cl_3SnCH_2CH_2COOC_4H_9$.

EXAMPLE 3

In a three-necked flask provided with stirrer, reflux condenser and bubble counter are introduced at 20° C. 37.9 parts of anhydrous Sn(II)chloride, 10.6 parts of acrylonitrile and 9.2 parts of formic acid in 70 parts of chloroform. There is then passed through the mixture, with stirring, hydrogen chloride gas, which is supplied in controlled amounts to ensure that the temperature does not exceed 40° C. Saturation with hydrogen chloride gas is attained after about 3 hours. The clear solution is freed in vacuo from the volatile constituents. The presence of

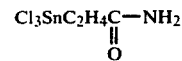

in the dry crystalline residue (496 parts) remaining can be verified by the $^1$HMR spectrum. Impurities can be removed by extraction with chloroform, so that finally an analytically pure product is obtained; melting point: 193° to 194° C.

The reaction proceeds according to the following equation:

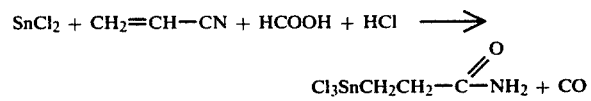

EXAMPLE 4

There are used in a reaction according to Example 3, instead of formic acid, 3.6 parts of $H_2O$ and 70 parts of dimethoxyethane as solvent. The reaction time is 3 hours and the reaction temperature is 35° C. The volatile constituents are removed to yield a solid residue which, after washing with chloroform constitutes pure

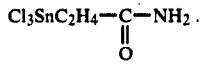

EXAMPLE 5

37.9 parts of anhydrous tin-II-chloride and 10.6 parts of acrylonitrile in 100 parts of concentrated HCl are placed into an apparatus according to Example 3. Hydrogen chloride gas is then passed into the mixture until saturation has been attained (about 4 hours), the temperature rising to about 50° C. The volatile constituents are subsequently removed in high vacuum to leave a waxlike residue which, according to the NMR-spectrum, is $Cl_3SnC_2H_4COOH$ (chemical shift of the carboxyl proton towards TMS in deuterised DMSO is 5.4 ppm). $Sn^{II}$ cannot be detected, which means that $SnCl_2$ has reacted quantitatively to give the desired organotin compound.

The reaction for producing organotin halides containing carboxyl groups is preferably performed in concentrated HCl as the reaction medium. It is also possible to perform the reaction in aqueous organic solvents.

We claim:

1. A process for the production of organotin compounds of the formula

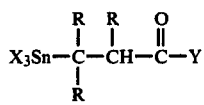

wherein

X is a chlorine, bromine or iodine atom, the

R's independently of one another are each a hydrogen atom or alkyl,

Y is OH, $NH_2$ or OR' in which R' is a hydrocarbon group of aliphatic, cycloaliphatic or aromatic character, or said group substituted by a hydroxyl, mercapto, alkoxy, alkylthio, carboxyl or carboalkoxy grup, which comprises reacting, at −30° C. to +100° C., a tin dihalide with hydrogen chloride, hydrogen bromide or hydrogen iodine and an unsaturated nitrile of the formula

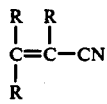

in a reactant medium selected from the group consisting of water, aqueous hydrochloric acid, water and alcohol, carboxylic acid, and alcohol with the proviso that when the reactant medium is alcohol the molar ratio of alcohol to nitrile is at least about 6:1.

2. A process according to claim 1 wherein the reactant medium is water, the molar ratio of water to nitrile is about 1:1 to 2:1, and a compound where Y is $NH_2$ is formed.

3. A process according to claim 1 wherein the reactant medium is water, the molar ratio of water to nitrile is greater than 2:1, and a compound where Y is OH is formed.

4. A process according to claim 1 wherein the reactant medium is aqueous hydrochloric acid, and a compound where Y is OH is formed.

5. A process according to claim 1 wherein the reactant medium is water and alcohol of formula R'OH, the molar ratio of water to alcohol is nitrile is about 1:1:1, and a compound where Y is OR' is formed.

6. A process according to claim 1 wherein the reactant medium is a carboxylic acid, the molar ratio of said acid to nitrile is at least about 1:1, and a compound where Y is $NH_2$ is formed.

7. A process according to claim 1 wherein the reactant medium is an alcohol of formula R'OH, the molar ratio of alcohol to nitrile is at least about 3:1, and a compound where Y is OR' is formed.

8. A process according to claim 1 wherein R is selected from the group consisting of a hydrogen atom and methyl.

9. A process according to claim 1, wherein X is a chlorine atom.

10. A process according to claim 1, wherein R is a hydrogen atom or alkyl having 1 to 4 C atoms.

11. A process according to claim 1, wherein the hydrocarbon group R' contains 1 to 12 carbon atoms.

12. A process according to claim 11, wherein the hydrocarbon group R' is straight-chain or branched-chain alkyl or cycloalkyl.

13. A process according to claim 1, wherein the unsaturated nitrile is acrylonitrile, methacrylonitrile, crotononitrile or β-dimethylacrylonitrile.

14. A process according to claim 1, wherein the reaction is performed without a solvent, or in the presence of an inert solvent having a halogen, ether, carboxylic acid ester or sulfone function.

15. A process according to claim 1, wherein the reaction is performed at a temperature of 20° to 50° C., and under normal pressure or under a slight excess pressure.

16. A process according to claim 1, wherein tin dichloride is reacted with acrylonitrile, n-butanol, water and hydrogen chloride to give β-n-butoxycarbonylethyl tin trichloride.

* * * * *

UNITED STATES PATENT AND TRADEMARK OFFICE
CERTIFICATE OF CORRECTION

PATENT NO. : 4,195,029
DATED : March 25, 1980
INVENTOR(S) : Eberhard Otto, et al.

It is certified that error appears in the above-identified patent and that said Letters Patent are hereby corrected as shown below:

Cover page, Item [30] Foreign Application Priority Data

"Nov. 14, 1977 [SE] Sweden ...............7713867"

should be

--Nov. 14, 1977 [CH] Switzerland .............. 13867/77--.

Signed and Sealed this

Eighth Day of July 1980

[SEAL]

Attest:

SIDNEY A. DIAMOND

Attesting Officer

Commissioner of Patents and Trademarks